US00PP08700P

United States Patent [19]

Christensen

[11] Patent Number: Plant 8,700

[45] Date of Patent: Apr. 26, 1994

[54] HYBRID TEA ROSE PLANT NAMED 'JACOLLY'

[75] Inventor: Jack E. Christensen, Ontario, Calif.

[73] Assignee: Bear Creek Gardens, Inc., Medford, Oreg.

[21] Appl. No.: 17,828

[22] Filed: Feb. 16, 1993

[51] Int. Cl.[5] ..... A01H 5/00

[52] U.S. Cl. ..... Plt./11

[58] Field of Search ..... Plt. 11, 15, 16, 17

[56] References Cited

U.S. PATENT DOCUMENTS

Plt. 4798 1/1982 Kordes ..... Plt./11

*Primary Examiner*—Howard J. Locker

*Attorney, Agent, or Firm*—Klarquist, Sparkman, Campbell, Leigh and Whinston

[57] ABSTRACT

A hybrid tea rose plant having distinctive orange flowers with a yellow reverse on the petals, red bark on main stems and laterals, thick petals, vigorous, upright growth habit, and an attractive exhibition-style flower and bud form.

1 Drawing Sheet

The present invention relates to a new and distinct variety of rose plant of the hybrid tea class which was originated by me by crossing an unnamed seedling with the variety Aroheddo.

The primary objective of this breeding was to produce a new rose variety having the good bud form of the female unnamed peach-colored seedling combined with the vigor, large flower and upright growth of the male parent. The objective was substantially achieved along with other desirable improvements as evidenced by the following unique combination of characteristics which are outstanding in the new variety and which distinguish it from its parents, as well as from all other varieties of which I am aware:

1. Distinctive orange flower with a yellow reverse on the petals;
2. Vigorous, upright habit;
3. Thick leathery petals;
4. Reddish bark on main stems and laterals; and
5. Exhibition-style bud and flower form.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—Aroheddo.

Classification:

*Botanical.*—Rosa hybrida.

*Commercial.*—Hybrid tea.

FLOWER

Observations made from specimens grown in a garden environment in Somis, Calif., from March through July, 1992.

Blooming habit: Recurrent.

Bud:

*Size.*—1½ inches when the petals start to unfurl.

*Form.*—Long, pointed ovoid.

*Color.*—When sepals first divide, bud color is Yellow Orange Group 14C. When half blown, the upper sides of the petals are Orange Red Group 32B changing to Orange Red Group 32A on the petal edges; and the lower sides of the petals are Yellow Orange Group 14C.

*Sepals.*—Color: Green Group 138C with a bronze red cast if exposed to bright hot sun. Surface texture: Covered in fine hairs. There are three lightly appendaged sepals. There are two unappendaged sepals with hairy edges.

*Receptacle.*—Color: Green Group 138B; often with reddish cast. Shape: Funnel. Size: Large (7/16×7/16 inches). Surface: Smooth.

*Peduncle.*—Length: Short (3 inches). Surface: Glandular. Color: Medium green and bronzy. Strength: Stiff, erect.

Bloom:

*Size.*—Large. Average open size is 4½ inches.

*Borne.*—Singly.

*Stems.*—Medium (14 to 18 inches).

*Form.*—When first open: High centered. Permanence: Retains its form to the end; outer petals curl back.

*Petalage.*—Number of petals under normal conditions: 30 to 35.

*Color.*—The upper side of the petals is Orange Red Group 32B changing to Orange Red Group 32A at petal margins. The reverse side of the petals is Yellow Orange Group 14C. The bases of the petals have a yellow half moon (¼×¼ inch) at the point of attachment. The major color on the upper side is Orange Red Group 32B.

*Variegations.*—Occasional greenish-white streak on the guard petals.

*Discoloration.*—No change in general tonality at the end of the first day. Little change at the end of the third day; petal edges will darken a little to Orange Red Group 32A.

*Fragrance.*—Slight.

Petals:

*Texture.*—Thick, leathery.

*Shape.*—Round.

*Form.*—Tips slightly recurved.

*Arrangement.*—Imbricated, with few petaloids in the center.

*Persistence.*—Drop off cleanly.

*Lastingness.*—On the plant: Long (5 to 6 days). As a cut flower: Long (7 days).

Reproductive parts:

*Anthers.*—Size: Medium. Quantity: Many. Color: Yellow. Arrangement: Regular round styles.

*Filaments.*—Color: Yellow.

*Pollen.*—Color: Gold yellow.

*Styles.*—Color: Red.

*Stigmas.*—Color: Greenish white.

Form: Bush.

Growth: Vigorous, upright, branching.

Foliage: Number of leaflets on normal mid-stem leaves: 5 or 7.

*Size.*—Large (6×4 inches).

*Quantity.*—Abundant.

*Color.*—New foliage: Reddish. Old foliage: Dark green, glossy.

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Rough, with prickles.

*Stipules.*—Medium, serrated.

*Disease resistance.*—Susceptible to mildew but resistant to rust under normal growing conditions at Somis, Calif.

Wood:

*New wood.*—Color: Reddish. Bark: Smooth.

*Old wood.*—Color: Brown. Bark: Smooth.

Prickles:

*Quantity.*—Many on main canes from base and on laterals from main canes.

*Form.*—Medium, hooked downward.

*Color when young.*—Red.

Small Prickles:

*Quantity.*—On main stalks: Many. On laterals: Many.

*Color.*—Brown.

I claim:

1. A new and distinct variety of rose plant of the hybrid tea class, substantially as herein shown and described, characterized particularly as to novelty by the unique combination of its distinctive orange flowers with a yellow reverse on the petals, red bark on main stems and laterals, thick petals, vigorous, upright growth habit, and an attractive exhibition-style flower and bud form.

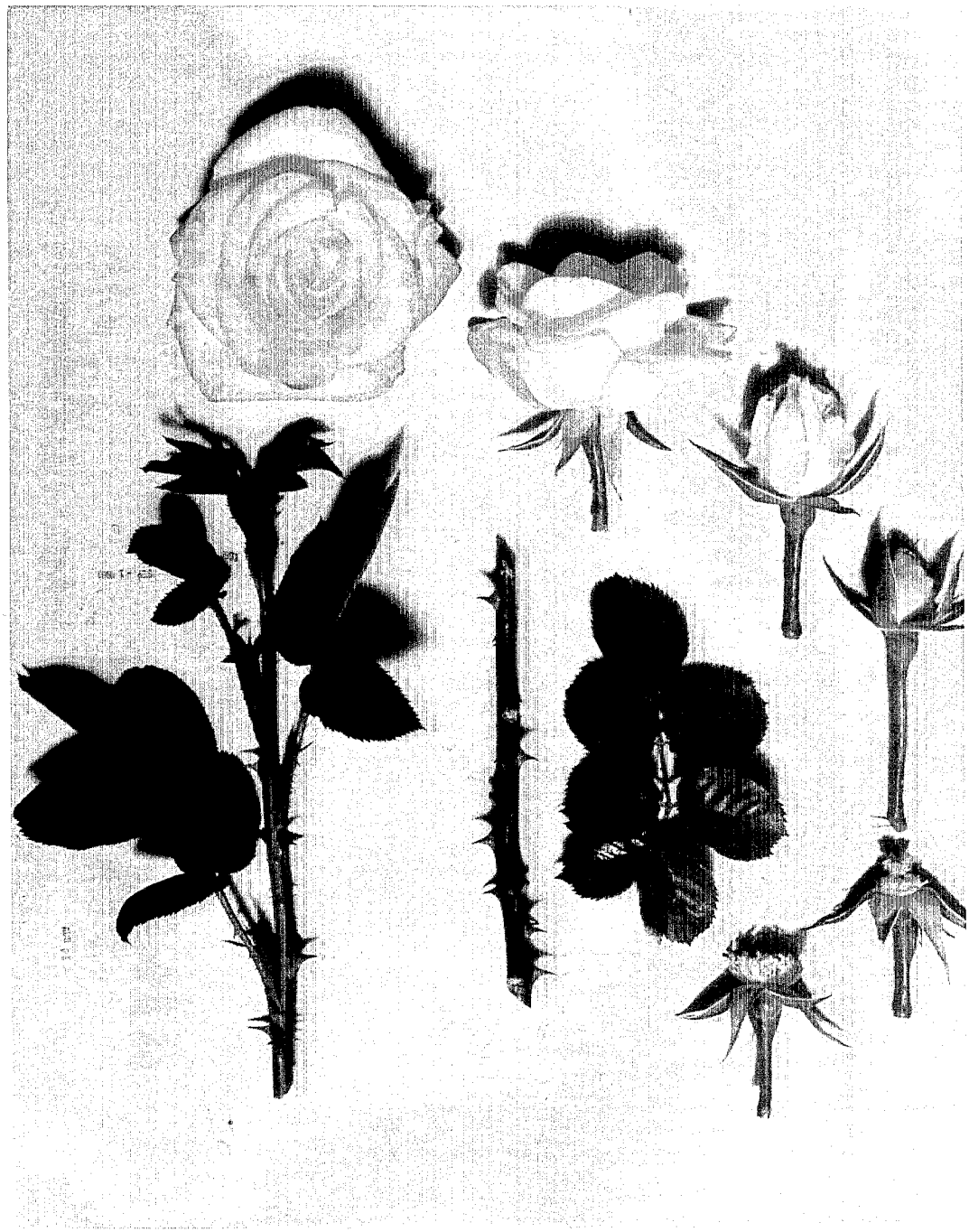

* * * * *